(12) United States Patent
Uta et al.

(10) Patent No.: US 9,920,080 B2
(45) Date of Patent: Mar. 20, 2018

(54) ALKOXYSILYL-VINYLENE GROUP-CONTAINING SILICON COMPOUND

(71) Applicant: SHIN-ETSU CHEMICAL CO., LTD., Tokyo (JP)

(72) Inventors: Akira Uta, Annaka (JP); Akitsugu Fujiwara, Annaka (JP); Takafumi Sakamoto, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/302,136

(22) PCT Filed: Feb. 2, 2015

(86) PCT No.: PCT/JP2015/052808
§ 371 (c)(1),
(2) Date: Oct. 5, 2016

(87) PCT Pub. No.: WO2015/159569
PCT Pub. Date: Oct. 22, 2015

(65) Prior Publication Data
US 2017/0190721 A1   Jul. 6, 2017

(30) Foreign Application Priority Data

Apr. 15, 2014  (JP) ................. 2014-083341

(51) Int. Cl.
C07F 7/04 (2006.01)
C07F 7/18 (2006.01)

(52) U.S. Cl.
CPC .................... C07F 7/1836 (2013.01)

(58) Field of Classification Search
CPC .................................... C07F 7/1836
USPC ......................................... 556/413
See application file for complete search history.

(56) References Cited

U.S. PATENT DOCUMENTS

| | | | |
|---|---|---|---|
| 3,555,051 | A | 1/1971 | Marsden et al. |
| 4,668,812 | A | 5/1987 | Quirk et al. |
| 5,030,746 | A | 7/1991 | Schilling, Jr. |
| 2005/0137361 | A1 | 6/2005 | Sakamoto et al. |
| 2006/0083851 | A1 | 4/2006 | Yan et al. |
| 2006/0084727 | A1 | 4/2006 | Yan et al. |

FOREIGN PATENT DOCUMENTS

| | | |
|---|---|---|
| JP | 50-28 A | 1/1975 |
| JP | 62-149687 A | 7/1987 |
| JP | 62-164688 A | 7/1987 |
| JP | 4-235190 | 8/1992 |
| JP | 9-12861 A | 1/1997 |
| JP | 2004-307723 A | 11/2004 |
| JP | 2006-156964 A | 6/2006 |
| JP | 2008-163143 A | 7/2008 |

OTHER PUBLICATIONS

Kujawa-Welten et al., Organometallics, 2002, vol. 21 (5), pp. 840-845.*
International Search Report dated Apr. 7, 2015 in PCT/JP2015/052808 filed Feb. 2, 2015.
Mario Beretta, et al., "Towards peptide formation inside the channels of a new divinylaniline-bridged periodic mesoporous organosilica", Chemical Communications, 2010, vol. 46, No. 14, p. 2495-2497.
Bogdan Marciniec, et al., "Synthesis, first structures, and catalytic activity of the monomeric rhodium(I)-siloxide phosphine complexes", Canadian Journal of Chemistry, 2003, vol. 81, No. 11, p. 1292-1298.
Stephane Jacob, et al., "Proton conducting inorganic-organic matrices based on sulfonyl- and styrene derivatives functionalized polycondensates via sol-gel processing", Electrochimica Acta, 2003, vol. 48, No. 14-16, p. 2181-2186.
Malgorzata Kujawa-Welten, et al., "Stereoselective synthesis of esters with vinylsilicon functionality via ruthenium carbine catalyzed cross-metathesis", Journal of Molecular Catalysis A: Chemical, 2002, vol. 190, No. 1-2, p. 79-83.
Malgorzata Kujawa-Welten, et al., "Cross-Metathesis of Vinylsilanes with Allyl Alkyl Ethers Catalyzed by Ruthenium-Carbene Complexes", Organometallics, 2002, vol. 21, No. 5, p. 840-845.
L. I. Kopylova, et al., "Hydrosilylation of 3-arylamino-1-butynes and their N-acyl derivatives", Zhurnal Obshchei Khimii, 1982, vol. 52, No. 10, 6 pages.
M. G. Voronkov, et al., "Synthesis of new derivatives of trans-1, 2-disilylethylene by hydrosilylation of ethynylsilanes", Izvestiya Akademii Nauk SSSR, Seriya Khimicheskaya, 1976, No. 8, 5 pages.
S. I. Sadykh-Zade, et al., "Synthesis of unsaturated silicon-containing epoxy compounds", Zhurnal Obshchei Khimii, 1966, vol. 36, No. 4, 4 pages.

(Continued)

*Primary Examiner* — Sudhakar Katakam
*Assistant Examiner* — Kofi Adzamli
(74) *Attorney, Agent, or Firm* — Oblon, McClelland, Maier & Neustadt, L.L.P.

(57) ABSTRACT

Provided is an alkoxysilyl-vinylene group-containing silicon compound represented by the following general formula (1):

[Chemical formula 1]

(1)

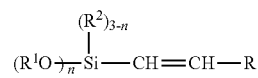

wherein each of $R^1$ and $R^2$ independently represents a monovalent hydrocarbon group having 1 to 20 carbon atoms; R represents a monovalent hydrocarbon group having an organic functional group(s) and 1 to 30 carbon atoms; and n represents an integer of 1 to 3.

The alkoxy groups in the novel organic silicon compound of the invention have a dramatically improved hydrolyzability. Further, a high adhesion or adhesiveness; and a fast adhesiveness can be exhibited by adding the novel organic silicon compound to a room temperature curable organopolysiloxane.

2 Claims, 3 Drawing Sheets

(56) References Cited

OTHER PUBLICATIONS

Extended European Search Report dated Aug. 2, 2017 in Patent Application No. 15780042.6.
S. I. Sadykh-Zade, et al., "Synthesis of unsaturated silicon-containing epoxide compounds", Zhurnal Obshchei Khimii, 1966, vol. 36, No. 4, 3 pages (submitting English translation only, non-English reference previously filed).
Japanese Office Action dated May 30, 2017 in Japanese Patent Application No. 2016-513653 (with English translation).

* cited by examiner

ALKOXYSILYL-VINYLENE GROUP-CONTAINING SILICON COMPOUND

TECHNICAL FIELD

The present invention relates to a novel organic silicon compound, especially to a novel alkoxysilyl-vinylene group-containing silicon compound useful as, for example, a silane coupling agent, a silylating agent and an adhesion aid.

BACKGROUND ART

Room temperature curable organopolysiloxanes have been widely used in, for example, the architecture field, the transportation field and the field of electrical and electronic parts, because they are safe and superior in durability and adhesion as rubbers.

Such room temperature curable organopolysiloxane is often required to have high adhesion for its intended purposes. Adhesion or adhesiveness of the room temperature curable organopolysiloxane to a base material has been improved by adding a carbon functional silane compound (so-called silane coupling agent) having an organic functional group(s) such as an amino group, an epoxy group, a methacryl group and a mercapto group.

As an amino group-containing alkoxysilane compound, there have been conventionally known, for example, γ-aminopropyltriethoxysilane, γ-aminopropyltrimethoxysilane, γ-aminopropylmethyl dimethoxysilane, γ-aminopropylmethyldiethoxysilane, N-β-aminoethyl-γ-aminopropylmethyl dimethoxysilane, N-benzyl-γ-aminopropyltrimethoxysilane, N-phenyl-γ-aminopropylmethoxysilane, β-aminoethylaminomethyl phenethyl trimethoxysilane and N-[m-aminomethylphenylmethyl]-γ-aminopropyltrimethoxysilane (Patent document 1). As an epoxy group-containing alkoxysilane compound, there have been known, for example, 2-(3,4-epoxycyclohexyl) ethyltrimethoxysilane, 3-glycidoxypropyltrimethoxysilane, 3-glycidoxypropylmethyldiethoxysilane and 3-glycidoxypropyltriethoxysilane (Patent document 2). As a methacryl group-containing alkoxysilane compound, there have been known, for example, 3-methacryloxypropyltrimethoxysilane, 3-methacryloxypropyltriethoxysilane, 3-methacryloxypropylmethyldimethoxysilane and 3-methacryloxypropylmethyldiethoxysilane (Patent document 3). As a mercapto group-containing alkoxysilane compound, there have been known, for example, 3-mercaptopropyltrimethoxysilane and 3-mercaptopropylmethyldimethoxysilane (Patent document 4). As described above, although many alkoxysilane compounds have been used as adhesion aids, there has been an increasing need, year after year, for improvement of the adhesion or adhesiveness to a base material.

PRIOR ART DOCUMENT

Patent Document

Patent document 1: JP-A-2008-163143
Patent document 2: JP-A-2004-307723
Patent document 3: JP-A-2006-156964
Patent document 4: JP-A-Hei-9-12861

SUMMARY OF THE INVENTION

Problems to be Solved by the Invention

The present invention has been made in view of the aforementioned concerns, and it is an object of the present invention to provide a novel organic silicon compound useful as, for example, a silane coupling agent, a silylating agent or an adhesion aid that is capable of improving the adhesion or adhesiveness to a base material.

Means to Solve the Problem

The inventors of the present invention diligently conducted a series of studies to achieve the above objective, and completed the invention as follows. That is, the inventors found that the hydrolyzability of alkoxy groups could be dramatically improved provided that the linking group adjacent to an alkoxysilyl group was a vinylene group, and that the adhesion or adhesiveness to a base material could be improved by using an organic silicon compound containing an alkoxysilyl-vinylene group(s), as represented by the following formula (1).

In short, the invention is to provide the following organic silicon compound.

<1>
An alkoxysilyl-vinylene group-containing silicon compound represented by the following general formula (1):

[Chemical formula 1]

(In the above formula, each of $R^1$ and $R^2$ independently represent a monovalent hydrocarbon group having 1 to 20 carbon atoms; R represents a monovalent hydrocarbon group having an organic functional group(s) and 1 to 30 carbon atoms; and n represents an integer of 1 to 3.)

In addition, an organooxy group and an organooxysilyl group that are respectively represented by $R^1O$— and $R^1O$—Si ($R^1$ represents a monovalent hydrocarbon group having 1 to 20 carbon atoms) may be described as an alkoxy group and an alkoxysilyl group hereunder. Further, an ethenylene represented by —CH═CH— may, for example, be described as a vinylene group hereunder.

Effects of the Invention

The novel organic silicon compound of the present invention exhibits a dramatically improved hydrolyzability of alkoxy groups due to the fact that the linking group adjacent to an alkoxysilyl group is a vinylene group. Moreover, a high adhesion or adhesiveness; and a fast adhesiveness can be exhibited by adding the novel organic silicon compound of the invention to a room temperature curable organopolysiloxane.

MODE FOR CARRYING OUT THE INVENTION

The present invention is described in greater detail hereunder.
<1>
A compound of the present invention is an alkoxysilyl-vinylene group-containing organic silicon compound represented by the following general formula (1)

[Chemical formula 2]

(1)

(In the above formula, each of $R^1$ and $R^2$ independently represents a monovalent hydrocarbon group having 1 to 20 carbon atoms; R represents a monovalent hydrocarbon group having an organic functional group(s) and 1 to 30 carbon atoms; and n represents an integer of 1 to 3.)

In the general formula (1), examples of the monovalent hydrocarbon group having 1 to 20 carbon atoms, as represented by $R^1$ and $R^2$, include an alkyl group such as a methyl group, an ethyl group, a propyl group, an isopropyl group, a butyl group, an isobutyl group, a tert-butyl group, a pentyl group, a hexyl group, a heptyl group, an octyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an eicosyl group; a cycloalkyl group such as a cyclopentyl group and a cyclohexyl group; an alkenyl group such as a vinyl group, an allyl group, a propenyl group and an isopropenyl group; an aryl group such as a phenyl group; and an aralkyl group such as a benzyl group and a phenylethyl group. Further, each of $R^1$ and $R^2$ may also be a linear hydrocarbon group having an alicyclic hydrocarbon group(s) or an aromatic hydrocarbon group(s). With regard to such monovalent hydrocarbon group represented by $R^1$ and $R^2$, a group having 1 to 10 carbon atoms is preferred, a group having 1 to 6 carbon atoms is more preferred, and a group having 1 or 2 carbon atom(s) (a lower alkyl group such as a methyl and an ethyl group or a lower alkenyl group such as a vinyl group) is particularly preferred.

Moreover, in general formula (1), examples of the organic functional group(s) contained in the monovalent hydrocarbon group that have 1 to 30, preferably 1 to 22 carbon atoms, as represented by R, include a (substituted) amino group, a glycidyl group, a mercapto group and a (metha) acryl group.

Examples of the group R include those represented by the following general formulae (2) to (9).

[Chemical formula 3]

—$R^3$—NH$_2$ (2)

—$R^3$—NH—$R^{3'}$—NH$_2$ (3)

—$R^3$—NH—$R^4$—NH$_2$ (4)

(5)

(6)

—$R^3$—O—C(=O)—CH=CH$_2$ (7)

—$R^3$—SH (8)

—$R^3$—NH—Ph (9)

(In the above formulae each of $R^3$ and $R^{3'}$ independently represents a divalent hydrocarbon group having 1 to 10, preferably 1 to 6, and more preferably 1 to 4 carbon atoms, and they may be the same or different; $R^4$ represents a divalent hydrocarbon group having 6 to 10 carbon atoms and having an aromatic ring(s); and Ph represents a phenyl group.)

Here, examples of the divalent hydrocarbon group represented by $R^3$ and $R^{3'}$ include linear or branched alkylene groups such as —CH$_2$—, —CH$_2$—CH$_2$—, —CH(CH$_3$)—, —CH$_2$—CH$_2$—CH$_2$—, —CH(CH$_3$)—CH$_2$—, —C(CH$_3$)$_2$—, —CH$_2$—CH$_2$—CH$_2$—CH$_2$—, —CH(CH$_3$)—CH$_2$—CH$_2$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CH(CH$_3$)(CH$_2$)$_4$—, —CH(CH$_3$)(CH$_2$)$_6$— and —CH(CH$_3$)(CH$_2$)$_8$—.

In the above general formula (4), examples of the divalent hydrocarbon group having 6 to 10 carbon atoms and having an aromatic ring(s), as represented by $R^4$, include a phenylene group and a group represented by the following formula (10).

[Chemical formula 4]

(10)

(Each of m and l independently represents an integer of 1 to 3)

Specific examples of $R^4$ include the following groups.

[Chemical formula 5]

Following are specific examples of the composition of the present invention.

[Chemical formula 6]

$(H_3CO)_3Si-CH=CH-CH_2-NH_2$
$(H_3CO)_3Si-CH=CH-CH_2-NH-CH_2-CH_2-NH_2$
$(H_3CO)_3Si-CH=CH-CH_2-NH-(CH_2)_4-NH_2$
$(H_3CO)_3Si-CH=CH-CH_2-NH-(CH_2)_6-NH_2$
$(H_3CO)_3Si-CH=CH-CH_2-NH-(CH_2)_8-NH_2$
$(H_3CO)_3Si-CH=CH-CH_2-NH-(CH_2)_{10}-NH_2$
$(H_3CO)_3Si-CH=CH-(CH_2)_2-NH-CH_2-CH_2-NH_2$
$(H_3CO)_3Si-CH=CH-(CH_2)_4-NH-CH_2-CH_2-NH_2$
$(H_3CO)_3Si-CH=CH-(CH_2)_6-NH-CH_2-CH_2-NH_2$
$(H_3CO)_3Si-CH=CH-(CH_2)_8-NH-CH_2-CH_2-NH_2$
$(H_3CO)_3Si-CH=CH-(CH_2)_{10}-NH-CH_2-CH_2-NH_2$
$(H_3CO)_3Si-CH=CH-(CH_2)_5-NH-(CH_2)_5-NH_2$ $(H_3CO)_3Si-CH=CH-CH_2-NH-\underset{\underset{CH_3}{|}}{CH}-CH_2-NH_2$ $(H_3CO)_3Si-CH=CH-\underset{\underset{CH_3}{|}}{CH}-NH-\underset{\underset{CH_3}{|}}{CH}-CH_2-NH_2$

[Chemical formula 7]

$(H_3CO)_3Si-CH=CH-CH_2-NH-\phantom{xxx}$ $(H_3CO)_3Si-CH=CH-CH_2-NH-CH_2-CH_2-\phantom{xxx}$

$(H_3CO)_3Si-CH=CH-CH_2-NH-CH_2-CH_2-\phantom{xxx}$ $(H_3CO)_3Si-CH=CH-\underset{\underset{CH_3}{|}}{CH}-NH-CH_2-\phantom{xxx}$ -continued

$(H_3CO)_3Si-CH=CH-(CH_2)_6-NH-\phantom{xxx}$

[Chemical formula 8]

$(H_3CO)_3Si-CH=CH-CH_2-O-CH_2-\underset{O}{\triangle}$
$(H_3CO)_3Si-CH=CH-(CH_2)_2-O-CH_2-\underset{O}{\triangle}$
$(H_3CO)_3Si-CH=CH-(CH_2)_2-O-CH_2-\underset{O}{\triangle}$
$(H_3CO)_3Si-CH=CH-(CH_2)_4-O-CH_2-\underset{O}{\triangle}$
$(H_3CO)_3Si-CH=CH-(CH_2)_6-O-CH_2-\underset{O}{\triangle}$
$(H_3CO)_3Si-CH=CH-(CH_2)_8-O-CH_2-\underset{O}{\triangle}$
$(H_3CO)_3Si-CH=CH-(CH_2)_{10}-O-CH_2-\underset{O}{\triangle}$

[Chemical formula 9]

[Chemical formula 10]

$(H_3CO)_3Si-CH=CH-CH_2-SH$
$(H_3CO)_3Si-CH=CH-(CH_2)_2-SH$
$(H_3CO)_3Si-CH=CH-(CH_2)_4-SH$

[Chemical formula 11]

$(H_3CO)_2\underset{\underset{CH_3}{|}}{Si}-CH=CH-CH_2-NH-CH_2-CH_2-NH_2$ $(H_3CO)_2\underset{\underset{CH_3}{|}}{Si}-CH=CH-CH_2-NH-(CH_2)_6-NH_2$

[Chemical formula 12]

$(H_3CO)_2$-Si(CH$_3$)-CH=CH-(CH$_2$)$_6$-NH-CH$_2$-CH$_2$-NH$_2$ $(H_3CO)_2$-Si(CH$_3$)-CH=CH-CH$_2$-NH-C$_6$H$_5$ $(H_3CO)_2$-Si(CH$_3$)-CH=CH-CH$_2$-NH-CH$_2$-C$_6$H$_4$-NH$_2$ $(H_3CO)_2$-Si(CH$_3$)-CH=CH-CH$_2$-NH-CH$_2$-CH$_2$-C$_6$H$_4$-CH$_2$-CH$_2$-NH$_2$

[Chemical formula 13]

$(H_3CO)_2$-Si(CH$_3$)-CH=CH-CH$_2$-O-CH$_2$-(epoxide)

$(H_3CO)_2$-Si(CH$_3$)-CH=CH-(CH$_2$)$_2$-O-CH$_2$-(epoxide)

[Chemical formula 14]

$(H_3CO)_2$-Si(CH$_3$)-CH=CH-(CH$_2$)$_2$-O-C(=O)-C(CH$_3$)=CH$_2$ $(H_3CO)_2$-Si(CH$_2$CH$_3$)-CH=CH-(CH$_2$)$_3$-O-C(=O)-C(CH$_3$)=CH$_2$

[Chemical formula 15]

$(H_3CO)_2$-Si(CH$_3$)-CH=CH-(CH$_2$)$_3$-SH $(H_3CO)_2$-Si(CH$_2$CH$_3$)-CH=CH-(CH$_2$)$_3$-SH

[Chemical formula 16]

H$_3$CO-Si(CH$_3$)$_2$-CH=CH-CH$_2$-NH-CH$_2$-CH$_2$-NH$_2$

H$_3$CO-Si(CH$_3$)$_2$-CH=CH-CH$_2$-NH-(CH$_2$)$_3$-NH$_2$

H$_3$CO-Si(CH$_3$)$_2$-CH=CH-(CH$_2$)$_2$-NH-CH$_2$-CH$_2$-NH$_2$

[Chemical formula 17]

H$_3$CO-Si(CH$_3$)$_2$-CH=CH-CH$_2$-NH-CH$_2$-C$_6$H$_4$-NH$_2$

H$_3$CO-Si(CH$_3$)$_2$-CH=CH-CH$_2$-NH-CH$_2$-C$_6$H$_4$-CH$_2$-CH$_2$-NH$_2$

H$_3$CO-Si(CH$_3$)$_2$-CH=CH-(CH$_2$)$_6$-NH-C$_6$H$_4$-NH$_2$

[Chemical formula 18]

H$_3$CO-Si(CH$_3$)$_2$-CH=CH-(CH$_2$)$_8$-O-CH$_2$-(epoxide)

H$_3$CO-Si(CH$_3$)$_2$-CH=CH-(CH$_2$)$_{10}$-O-CH$_2$-(epoxide)

[Chemical formula 19]

H$_3$CO-Si(CH$_3$)$_2$-CH=CH-(CH$_2$)$_2$-O-C(CH$_3$)$_2$-C(=O)-C(CH$_3$)=CH$_2$

H$_3$CO-Si(CH$_3$)(CH$_2$CH$_3$)-CH=CH-(CH$_2$)$_5$-O-C(CH$_3$)$_2$-C(=O)-C(CH$_3$)=CH$_2$

H$_3$CO-Si(CH$_2$CH$_3$)$_2$-CH=CH-(CH$_2$)$_9$-O-C(CH$_3$)$_2$-C(=O)-C(CH$_3$)=CH$_2$

[Chemical formula 20]

H$_3$CO-Si(CH$_3$)$_2$-CH=CH-(CH$_2$)$_3$-SH

[Chemical formula 21]

$(H_3CH_2CO)_3$-Si-CH=CH-CH$_2$-NH$_2$ $(H_3CH_2CO)_3$-Si-CH=CH-CH$_2$-NH-CH$_2$-CH$_2$-NH$_2$ $(H_3CH_2CO)_3$-Si-CH=CH-CH$_2$-NH-(CH$_2$)$_{10}$-NH$_2$ $(H_3CH_2CO)_3$-Si-CH=CH-(CH$_2$)$_5$-NH-(CH$_2$)$_5$-NH$_2$ $(H_3CH_2CO)_3$-Si-CH=CH-CH$_2$-NH-CH(CH$_3$)-CH(CH$_3$)-NH$_2$

[Chemical formula 22]

$(H_3CH_2CO)_3$-Si-CH=CH-CH$_2$-NH-C$_6$H$_5$ $(H_3CH_2CO)_3$-Si-CH=CH-CH$_2$-NH-C$_6$H$_4$-NH$_2$ $(H_3CH_2CO)_3$-Si-CH=CH-CH$_2$-NH-CH$_2$-C$_6$H$_4$-CH$_2$-NH$_2$

$(H_3CH_2CO)_3$-Si-CH=CH-(CH$_2$)$_4$-NH-CH$_2$-C$_6$H$_4$-NH$_2$

$(H_3CH_2CO)_3$-Si-CH=CH-(CH$_2$)$_6$-NH-C$_6$H$_5$

[Chemical formula 23]

$(H_3CH_2CO)_3$-Si-CH=CH-CH$_2$-O-CH$_2$-(epoxide)

-continued

[Chemical formula 24]

[Chemical formula 25]

[Chemical formula 26]

[Chemical formula 27]

[Chemical formula 28]

[Chemical formula 29]

[Chemical formula 30]

[Chemical formula 31]

[Chemical formula 32]

[Chemical formula 33]

[Chemical formula 34]

[Chemical formula 35]

The compound of the present invention having an amino group at its terminal end can be synthesized as follows.

That is, such compound of the invention can be obtained by reacting a halogenoalkoxysilane represented by the general formula bellow and a diamine represented by the general formula $H_2N-R^{3'}-NH_2$ or $H_2N-R^4-NH_2$ at a molar ratio of diamine to silane of not smaller than 0.5, more preferably not smaller than 1.0, at a temperature of 50 to 200° C., preferably 80 to 150° C. for about 30 min to 30 hours. Here, $R^{3'}$ and $R^4$ are identical to those defined earlier.

[Chemical formula 36]

(In the above formula, $R^1$, $R^2$ and $R^3$ are identical to those defined earlier; and X represents a halogen atom)

There, the diamine component may be used as a hydrogen halide scavenger, and tertiary amine compounds such as trimethylamine, triethylamine, tributylamine and pyridine may be used as other hydrogen halide scavenger. Further, the resulting hydrogen halide salt may also be neutralized by a sodium alkoxide.

The compound of the present invention having a mercapto group at its terminal end can be synthesized as follows.

That is, such compound of the invention can be obtained by reacting a halogenoalkoxysilane represented by the general formula bellow and a thiourea at a molar ratio of thiourea to silane of not smaller than 0.5, more preferably not smaller than 1.0, at a temperature of 50 to 200° C., preferably 80 to 150° C. for about 30 min to 30 hours, and then by reacting an isothiourea salt thus generated and a base for 1 to 10 hours.

[Chemical formula 37]

(In the above formula, $R^1$, $R^2$, $R^3$ and X are identical to those defined earlier.)

It is preferred that the base used here be that having a low reactivity with alkoxysilane. Examples of this base include an amine compound such as trimethylamine, triethylamine, tributylamine, pyridine, N, N-diethylamine, N, N-dimethylamine and ammonia; and an alkoxide compound such as sodium methoxide and sodium ethoxide.

The compound of the present invention having a glycidyl group at its terminal end can be synthesized as follows.

That is, such compound of the invention can be obtained by reacting an alkoxysilyl compound (alkoxyhydrosilane) and a glycidyl compound which are represented by the general formulae bellow, under the presence of a platinum-group metal catalyst. There, it is preferred that the reaction be performed at a molar ratio of the alkoxysilyl compound to the glycidyl compound of 0.5 to 2.0, more preferably 1.0 to 1.5, at a temperature of 40 to 200° C., preferably 60 to 120° C. for about 30 min to 15 hours.

[Chemical formula 38]

(In the above formula, $R^1$, $R^2$ and n are identical to those defined earlier.)

[Chemical formula 39]

(In the above formula, $R^3$ and $R^{3'}$ are identical to those define earlier.)

Examples of the platinum-group metal catalyst used here include a chloroplatinic acid; an alcohol solution of a chloroplatinic acid; a reactant of a chloroplatinic acid and an alcohol; a platinum-olefin complex compound; a platinum-vinyl group-containing siloxane complex; and a platinum-supported carbon.

Further, the compound of the present invention having a (metha) acrylic group (i.e. acrylic group or methacrylic group) at its terminal end can, for example, be synthesized as follows.

That is, such compound of the invention can be obtained by reacting an alkoxysilyl compound (alkoxyhydrosilane) and a (metha) acrylic compound (referred to as methacrylic compound) which are represented by the general formulae bellow, under the presence of a platinum-group metal catalyst.

There, it is preferred that the reaction be performed at a molar ratio of the alkoxysilyl compound to the methacrylic compound of 0.5 to 2.0, more preferably 1.0 to 1.5, at a temperature of 40 to 200° C., preferably 60 to 120° C. for about 30 min to 15 hours.

[Chemical formula 40]

(In the above formula, $R^1$, $R^2$ and n are identical to those defined earlier.)

[Chemical formula 41]

(In the above formula, $R^3$ is identical to that defined earlier.)

A polymerization inhibitor may also be added at the time of performing the above reaction in order to prevent polymerization of methacrylic groups. Examples of such polymerization inhibitor include 1,3,5-trimethyl-2,4,6-tris (3,5-di-t-butyl-4-hydroxybenzyl) benzene (product name: IRGANOX 1330); 2,6-di-t-butyl-4-methylphenol (product name: Sumilizer BHT); 2,5-di-t-butyl-hydroquinone (product name: Nocrac NS-7); 2,6-di-t-butyl-4-ethylphenol (product name: Nocrac M-17); 2,5-di-t-amylhydroquinone (product name: Nocrac DAH); 2,2'-methylenebis (4-methyl-6-t-butylphenol) (product name: Nocrac NS-6); 3,5-di-t-butyl-4-hydroxy-benzyl phosphonate-diethyl ester (product name: IRGANOX 1222); 4,4'-thiobis (3-methyl-6-t-butyl-phenol) (product name: Nocrac 300); 2,2'-methylenebis (4-ethyl-6-t-butylphenol) (product name: Nocrac NS-5); 4,4'-butylidenebis (3-methyl-6-t-butylphenol) (product name ADK STAB AO-40); and 2-t-butyl-6-(3-t-butyl-2-hydroxy-5-methylbenzyl)-4-methylphenylacrylate (product name: Sumilizer GM).

Further, catalysts similar to those used in the above reactions may be used as platinum-group metal catalysts.

Further, in any one of the above synthetic methods, a solvent may be added at the time of reaction. Here, there are no particular restrictions on such solvent. Examples of this solvent include aromatic hydrocarbons such as toluene, xylene and benzene; aliphatic hydrocarbons such as pentane, hexane, heptane, nonane, octane and decane; ethers such as dimethylether, methylethyl ether, tetrahydrofuran and dioxane; alcohols such as methanol and ethanol; halogenated hydrocarbons such as perchloroethane, perchloroethylene, trichloroethane, chloroform and carbon tetrachloride; amides such as dimethylformamide; and esters such as ethyl acetate, methyl acetate and butyl acetate.

WORKING EXAMPLE

A synthetic method of the compound of the present invention is described in detail hereunder with reference to working examples (synthetic examples). However, the compound of the invention is not limited to the following examples.

Working Example 1

(1) Production of 3-chloro-1-propenyltrimethoxysilane

Figure 1:
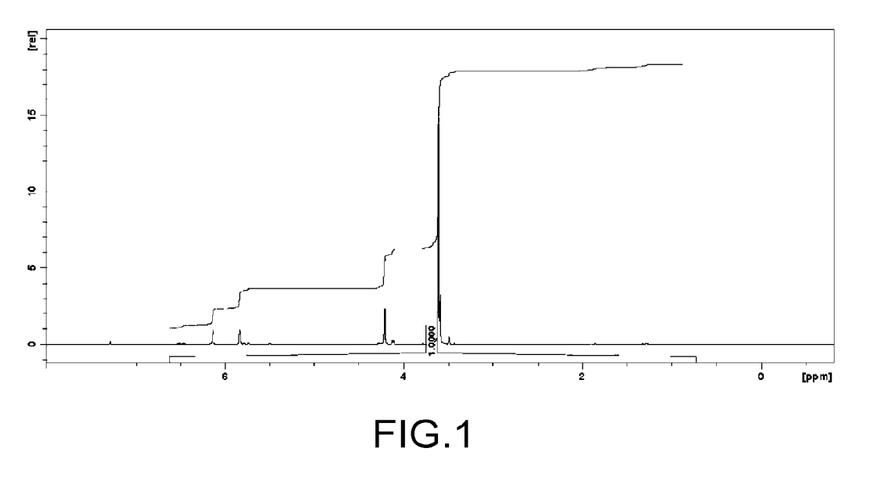
FIG. 1 is a diagram showing a $^1$H-NMR spectrum of a compound obtained in working example 1 (1).

A 80% propargyl chloride toluene solution of an amount of 250 mL (2.3 mol) and a 0.5 wt % chloroplatinic acid toluene solution of an amount of 5.0 g were placed in a 1 L separable flask having a stirrer, a thermometer, a reflux condenser and a dispensing device, followed by heating the same to 70° C. under a nitrogen atmosphere. Trimethoxysilane of 337.0 g (2.76 mol) was placed in the dispensing device, and was then delivered by drops while controlling a dropping rate in a way such that the solution temperature became 70 to 80° C. After completing dropping the trimethoxysilane, the temperature of the reaction solution was maintained at 80° C. for two hours. By distilling the reaction solution at 80° C. under 15 mmHg, there was obtained 269 g (yield 58%) of a final product as a mixture of multiple isomers. These isomers were then analyzed through $^1$H-NMR spectrum measurement, and it was confirmed that the final product was a 3-chloropropa-1-enyltrimethoxysilane having two isomers at a molar ratio of 1:0.08. FIG. 1 is a $^1$H-NMR spectrum chart of the synthesized 3-chloropropa-1-enyltrimethoxysilane.

(2) Production of N-2-(aminoethyl)-3-amino-1-propenyltrimethoxysilane

An ethylenediamine of an amount of 121.6 g (2.0 mol) was placed in a 500 mL three-necked flask having a stirrer, a thermometer, a reflux condenser and a dispensing device, followed by heating the same to 100° C. under a nitrogen atmosphere. A 3-chloropropa-1-enyltrimethoxysilane of 100 g (0.5 mol) was placed in the dispensing device, and was then delivered by drops while controlling a dropping rate in a way such that the solution temperature was within a range of 100 to 105° C.

Figure 2:
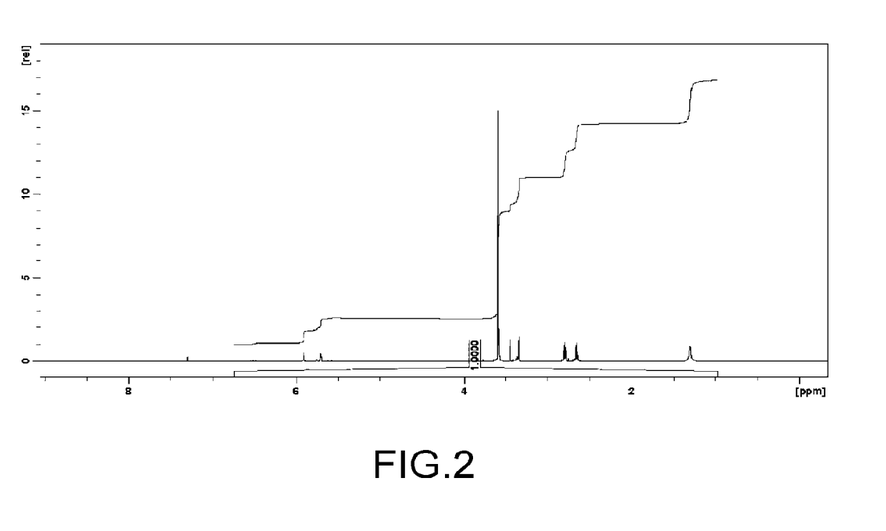
FIG. 2 is a diagram showing a $^1$H-NMR spectrum of a compound obtained in working example 1 (2) of the present invention.

After completing dropping the 3-chloropropa-1-enyltrimethoxysilane, the temperature of the reaction solution was maintained at 100° C. for two hours, followed by cooling the same. The reaction solution was then moved to a separating funnel to eliminate a triethylamine hydrochloride in a lower layer, followed by distilling the reaction solution at 150° C. under 15 mmHg into 78 g (yield 60%) of a final product as a mixture of multiple isomers. These isomers were then analyzed through $^1$H-NMR spectrum measurement, and it was confirmed that the final product was an N-2-(aminoethyl)-3-aminopropa-1-enyltrimethoxysilane having two isomers at a molar ratio of 1:0.08. FIG. 2 is a $^1$H-NMR spectrum chart of the synthesized N-2-(aminoethyl)-3-aminopropa-1-enyltrimethoxysilane.

Working Example 2

Figure 3:
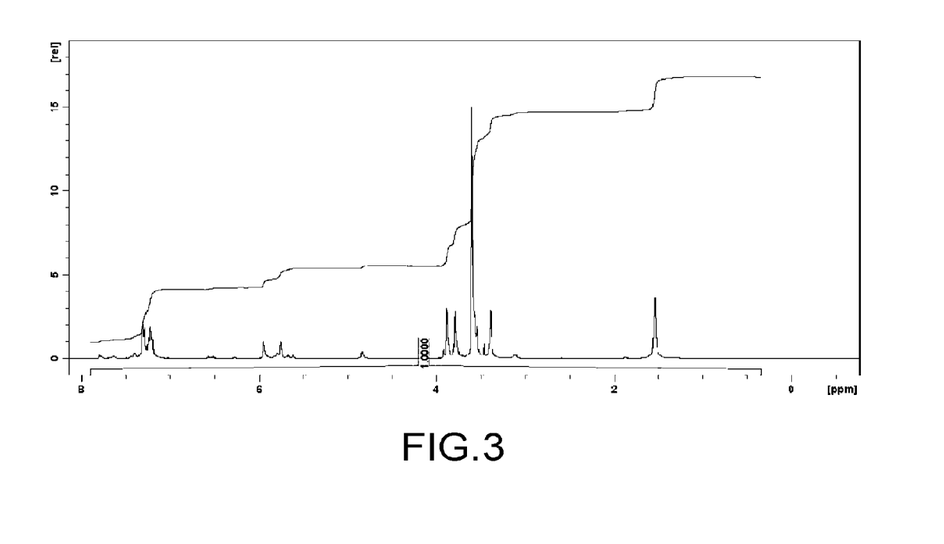
FIG. 3 is a diagram showing a $^1$H-NMR spectrum of a compound obtained in working example 2 of the present invention.

Production of N-[m-(aminomethylphenyl)methyl)]-γ-amino-1-propenyltrimethoxysilane An m-xylenediamine of an amount of 272.4 g (2.0 mol) and a xylene of 200 mL were placed in a 1 L three-necked flask having a stirrer, a thermometer, a reflux condenser and a dispensing device, followed by heating the same to 100° C. under a nitrogen atmosphere. A 3-chloropropa-1-enyltrimethoxysilane of 100 g (0.5 mol) was placed in the dispensing device, and was then delivered by drops while controlling a dropping rate in a way such that the solution temperature was within a range of 110 to 120° C. After completing dropping the 3-chloropropa-1-enyltrimethoxysilane, the temperature of the reaction solution was maintained at 120° C. for 5 hours, followed by cooling the same to 60° C. Next, a 28% sodium methoxide methanol solution of 91.6 g (0.48 mol) was delivered by drops thereinto, and the solution was continuously stirred for an hour while maintaining the solution temperature at 60° C. After completing stirring, the solution was cooled and then filtrated so as to separate therefrom a sodium chloride as a by-product. As a result of vacuum concentrating such filtrated solution at 150° C. under 3 mmHg, there was obtained a yellow and transparent liquid of 134.4 g (yield 80%). This compound was then analyzed through $^1$H-NMR spectrum measurement, and it was confirmed that the compound was an N-[m-(aminomethylphenyl)methyl)]-γ-aminopropa-1-enyltrimethoxysilane having two isomers at a molar ratio of 1:0.08. FIG. 3 is a $^1$H-NMR spectrum chart of the synthesized N-[m-(aminomethylphenyl)methyl)]-γ-aminopropa-1-enyltrimethoxysilane.

Working Example 3

(1) Production of Propargyl Glycidyl Ether

Figure 4:
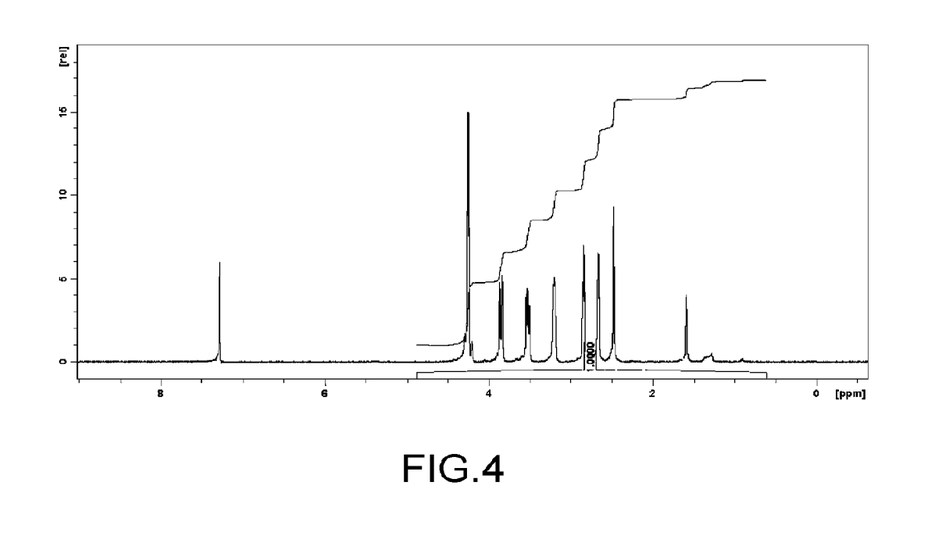
FIG. 4 is a diagram showing a $^1$H-NMR spectrum of a compound obtained in working example 3 (1).

A propargyl alcohol of an amount of 166.2 g (3.0 mol) and a tin chloride of 0.7 g (0.01 mol) were placed in a 1 L three-necked flask having a stirrer, a thermometer, a reflux condenser and a dispensing device, followed by heating the same to 100° C. under a nitrogen atmosphere. An epichlorohydrin of 92.5 g (1.0 mol) was placed in the dispensing device, and was then delivered by drops while controlling a dropping rate in a way such that the solution temperature was within a range of 95 to 105° C. After completing dropping the epichlorohydrin, the solution was reacted for 20 hours while being maintained at 100° C. Next, after cooling the reaction solution to 90° C., a 16 wt % sodium hydroxide aqueous solution of 325 g (3 mol) was added thereto, followed by reacting the solution for 6 hours. After the reaction had been finished, the solution was cooled, and then moved to a separating funnel. After washing the solution three times with a pure water of 100 mL, an anhydrous sodium sulfate was used to perform dehydration. The anhydrous sodium sulfate was them eliminated by filtration, followed by performing distillation at 110° C. under 15 mmHg to obtain 45 g (yield 40%) of a transparent liquid. This compound was then analyzed through $^1$H-NMR spectrum measurement, and it was confirmed that the compound was propargyl glycidyl ether. FIG. 4 is a $^1$H-NMR spectrum chart of the synthesized propargyl glycidyl ether.

(2) Production of 3-glycidoxy-1-propenyltrimethoxysilane

Figure 5:
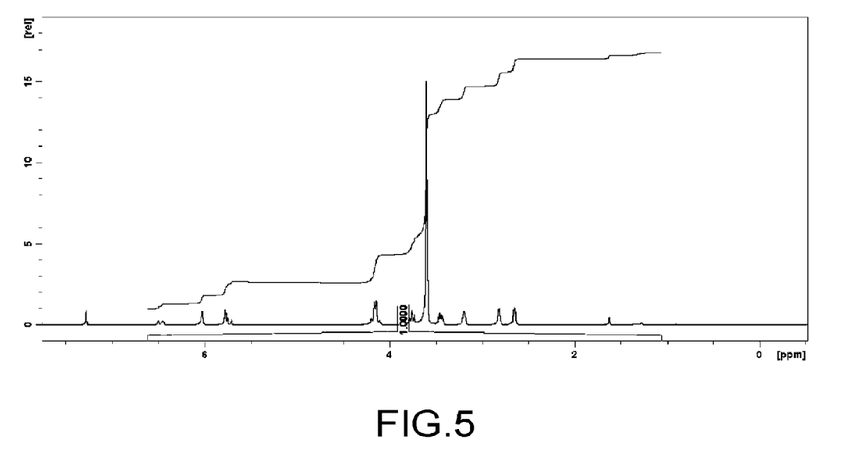
FIG. 5 is a diagram showing a $^1$H-NMR spectrum of a compound obtained in working example 3 (2) of the present invention.

A propargyl glycidyl ether of an amount of 45 g (0.4 mol) and a 0.5 wt % chloroplatinic acid toluene solution of an amount of 0.1 g were placed in a 200 mL three-necked flask having a stirrer, a thermometer, a reflux condenser and a dispensing device, followed by heating the same to 70° C. under a nitrogen atmosphere. A trimethoxysilane of 58 g (0.48 mol) was placed in the dispensing device, and was then delivered by drops while controlling a dropping rate in a way such that the solution temperature was within a range of 70 to 80° C. After completing dropping the trimethoxysilane, the temperature of the reaction solution was maintained at 80° C. for 5 hours. Distillation was then performed at 150° C. under 15 mmHg to obtain 56.2 g (yield 60%) of a final product as a mixture of multiple isomers. These isomers were then analyzed through $^1$H-NMR spectrum measurement, and it was confirmed that the final product was a 3-glycidoxypropa-1-enyltrimethoxysilane having two isomers at a molar ratio of 1:0.22. FIG. 5 is a $^1$H-NMR spectrum chart of the synthesized 3-glycidoxypropa-1-enyltrimethoxysilane.

REFERENCE EXAMPLE

Described hereunder are reference examples where the organic silicon compound of the invention was used as an adhesion aid. Hereunder, "parts" means "parts by mass".

Reference Example 1

A dimethylpolysiloxane of an amount of 100 parts and an atomized silica of an amount of 15 parts were homogenously mixed together, such dimethylpolysiloxane having a viscosity of 20,000 mPa·s and a molecular chain whose terminal ends are both blocked by silanol groups, and such atomized silica being surface-treated by dimethyldichlorosilane. Further added thereto were 0.6 parts of a tetramethylguanidyl-propyltrimethoxysilane; 5 parts of ethylhexyl 2-(dimethoxymethylsilyl) propanoate; 0.6 parts of dibutyltin dilaurate; and 0.5 parts of N-2-(aminoethyl)-3-amino-1-propenyltrimethoxysilane (working example 1 (2)), followed by performing mixing under no moisture condition until the components had been uniformly mixed together. A composition was thus prepared.

Reference Example 2

A composition was prepared in a similar manner as reference example 1 except that 0.5 parts of an N-[m-(aminomethylphenyl)methyl)]-γ-amino-1-propenyltrimethoxysilane were used (working example 2) instead of the N-2-(aminoethyl)-3-amino-1-propenyltrimethoxysilane.

Comparative Reference Example 1

A composition was prepared in a similar manner as reference example 1 except that 0.5 parts of an N-2-(aminoethyl)-3-aminopropyltrimethoxysilane were used instead of the N-2-(aminoethyl)-3-amino-1-propenyltrimethoxysilane.

Comparative Reference Example 2

A composition was prepared in a similar manner as reference example 1 except that 0.5 parts of an N-[m-(aminomethylphenyl)methyl)]-γ-aminopropyltrimethoxysilane were used instead of the N-2-(aminoethyl)-3-amino-1-propenyltrimethoxysilane.

A specimen was then prepared as follows. That is, a spatula was used to form each composition into a shape of W 10 mm×L 50 mm×T 2 mm on an adherend, immediately after the composition had been prepared in each reference example and each comparative reference example. After keeping this specimen under the following conditions, a cured product thereof was cut by a knife, followed by peeling off the cut portion by hand (nipped and then pulled by hand), and then observing the peeling state (hand peeling test via knife cuts). In this way, an adhesive interface between the adherend and the composition was able to be evaluated.

An initial adhesion was evaluated after completing keeping at a temperature of 23° C. and a relative humidity of 50% for 48 hours.

The evaluation was performed based on a percentage of an area of the composition where cohesive failure had occurred. When such percentage was 100%, the specimens were marked "⊚"; when such percentage was not lower than 80% but lower than 100%, the specimens were marked "○"; when such percentage was not lower than 50% but lower than 80%, the specimens were marked "Δ"; and when such percentage was lower than 50%, the specimens were marked "×." The results thereof are shown in Table 1.

TABLE 1

| | Reference example 1 | Reference example 2 | Comparative reference example 1 | Comparative reference example 2 |
|---|---|---|---|---|
| ABS | ○ | ⊚ | X | Δ |
| PBT | Δ | ○ | X | ○ |
| SUS | ⊚ | ○ | Δ | X |

According to the results of the above simple adhesion test, it was confirmed that an adhesion or adhesiveness to a base material could be exhibited in a short period of time by adding the alkoxysilyl-vinylene group-containing silicon compound of the invention to a room temperature curable organopolysiloxane, and that the alkoxysilyl-vinylene group-containing silicon compound of the invention was significantly useful as an adhesion aid to a room temperature curable organopolysiloxane.

The invention claimed is:
1. An alkoxysilyl-vinylene group-containing silicon compound represented by formula (1):

wherein each of $R^1$ and $R^2$ independently represents a monovalent hydrocarbon group having 1 to 20 carbon atoms; R represents a group selected from the groups expressed by formulae (3) and (4):

wherein $R^3$ represents an identical or different divalent hydrocarbon group having 1 to 10 carbon atoms; $R^{3'}$ represents an alkylene group having 1 to 10 carbon atoms; $R^4$ represents a divalent hydrocarbon group having an aromatic ring(s) and 6 to 10 carbon atoms; and n represents an integer of 1 to 3.

2. The alkoxysilyl-vinylene group-containing silicon compound according to claim 1, wherein $R^4$ in formula (4) is represented by formula (10):

wherein each of m and l independently represents an integer of 1 to 3.

* * * * *